United States Patent [19]
Kirishiki et al.

[11] Patent Number: 5,741,948
[45] Date of Patent: Apr. 21, 1998

[54] PROCESS FOR PRODUCTION OF (POLY) ALKYLENE GLYCOL MONOALKYL ETHER

[75] Inventors: Masaru Kirishiki, Suita; Yukio Kadono, Yokohama; Isamu Maeda, Mishima-gun; Yasuhiko Satoh, Yokohama; Fumiaki Morishita; Yoshiyuki Onda, both of Suita; Hideaki Tsuneki, Tokyo, all of Japan

[73] Assignee: Nippon Shokubai Co., Ltd., Osaka, Japan

[21] Appl. No.: 659,350

[22] Filed: Jun. 6, 1996

[30] Foreign Application Priority Data

Jun. 8, 1995 [JP] Japan ................... 7-141881

[51] Int. Cl.$^6$ ................................. C07C 41/01
[52] U.S. Cl. ................. 568/619; 502/71; 502/77; 502/79
[58] Field of Search .............. 568/619; 502/71, 502/77, 78, 79

[56] References Cited

U.S. PATENT DOCUMENTS

| | | |
|---|---|---|
| 4,368,337 | 1/1983 | Tawara et al. . |
| 4,725,494 | 2/1988 | Paxson et al. . |

FOREIGN PATENT DOCUMENTS

| | | |
|---|---|---|
| 0407841A2 | 1/1991 | European Pat. Off. . |
| 4222183A1 | 1/1994 | Germany . |

OTHER PUBLICATIONS

London, GB Week 9118; AN 91-125322 "Synthesis of low mol. wt. glycol ether(s)" XP002013322.

*Primary Examiner*—Gary Geist
*Assistant Examiner*—Sreeni Padmanabhan
*Attorney, Agent, or Firm*—Sherman and Shalloway

[57] ABSTRACT

There is provided a process for producing a (poly)alkylene glycol monoalkyl ether from an olefin and a (poly)alkylene glycol at a high conversion at a high selectivity. This process comprises reacting an olefin with a (poly)alkylene glycol in the presence of a crystalline metallosilicate as a catalyst.

7 Claims, No Drawings

PROCESS FOR PRODUCTION OF (POLY) ALKYLENE GLYCOL MONOALKYL ETHER

The present invention relates to a process for producing a (poly)alkylene glycol monoalkyl ether. More particularly, the present invention relates to a process for producing a (poly)alkylene glycol monoalkyl ether by reacting an olefin with a (poly)alkylene glycol.

(Poly)alkylene glycol monoalkyl ethers are useful as a solvent, a surfactant or an intermediate for production thereof. In particular, (poly)ethylene glycol monoalkyl ethers obtained from a long-chain olefin having many carbon atoms, generally have good wetting power, good solubilizing power and a low pour point and therefore have excellent functions as a surfactant.

With respect to the production of a (poly)alkylene glycol monoalkyl ether by the reaction of an olefin with a (poly)alkylene glycol, various processes such as shown below were proposed.

In, for example, Japanese Patent Publication Nos. 35687/1982, 34935/1985 and 17574/1987 and Japanese Patent Application Kokai (Laid-Open) No. 295941/1990 are disclosed processes of reacting an olefin with a (poly)alkylene glycol in the presence of a strongly acidic cation exchange resin as a catalyst to produce a (poly)alkylene glycol monoalkyl ether.

In, for example, Japanese Patent Application Kokai (Laid-Open) No. 148233/1991 are disclosed processes of reacting an olefin with a (poly)alkylene glycol in the presence of a heteropoly-acid as a catalyst to produce a (poly)alkylene glycol monoalkyl ether.

In, for example, Japanese Patent Publication No. 51570/1986 are disclosed processes of reacting an olefin with a (poly)alkylene glycol in the presence of benzenesulfonic acid or toluenesulfonic acid as a catalyst to produce a (poly)alkylene glycol monoalkyl ether.

However, in the above addition reaction between an olefin and a (poly)alkylene glycol in the presence of a strongly acidic cation exchange resin, a heteropoly-acid, benzenesulfonic acid or toluenesulfonic acid, the reaction rate is low, making the olefin conversion low and, moreover, the selectivity from olefin to (poly)alkylene glycol monoalkyl ether is low. The reaction rate is lower as the olefin as one raw material has higher carbon number. Further, the (poly)alkylene glycol as other raw material, which is a dihydric alcohol, per se causes, during the addition reaction, side reactions such as dehydration and polycondensation, cyclodehydration and the like, making very low the selectivity of the addition reaction with olefin.

The object of the present invention is to solve the above-mentioned problems of the prior art and provide a process which can produce a (poly)alkylene glycol monoalkyl ether at a high selectivity at a high yield in industry.

The present inventors made a study in order to achieve the above object. As a result, the present inventors found out that when a crystalline metallosilicate is used as a catalyst, the reaction rate between olefin and (poly)alkylene glycol is high, the side reactions of (poly)alkylene glycol per se can be suppressed, and a (poly)alkylene glycol monoalkyl ether can be produced efficiently at a high selectivity.

According to the present invention, there is provided a process for producing a (poly)alkylene glycol monoalkyl ether, which comprises reacting an olefin with a (poly) alkylene glycol in the presence of a crystalline metallosilicate as a catalyst.

The olefin used in the present invention includes hydrocarbons of 2–40 carbon atoms, each having an ethylenically unsaturated bond(s), preferably noncyclic hydrocarbons of 6–30 carbons, each having an ethylenically unsaturated bond(s). The olefin specifically includes ethylene, propylene, butene, isobutylene, butadiene, hexene, octene, decene, dodecene, tetradecene, hexadecene, octadecene, eicosene, etc. They may be used singly or in admixture of two or more. Of these, particularly preferred are olefins having many carbon atoms, such as octene, decene, dodecene, tetradecene, hexadecene, octadecene, eicosene and the like. In these olefins, the position(s) of the unsaturated bond(s) may be an α-position, an inner position, or an α-position and an inner position. It is of course possible to use, in combination, two or more olefins whose unsaturated bond positions are different from each other. In the reaction step of the present process, there arises, besides the intended reaction, the shift of the unsaturated bond(s) of the olefin, i.e. the isomerization of the olefin. In general, inner olefins, as compared with α-olefins, are stable thermodynamically; therefore, when an α-olefin is used as a raw material in the above reaction, it is gradually isomerized in to an inner olefin. The rate of the isomerization varies depending upon the reaction temperature and the kind and amount of the crystalline metallosilicate used as a catalyst. A (poly) alkylene glycol monoalkyl ether obtained from the above-mentioned noncyclic olefin of 6–30 carbon atoms is suitable as a material for surfactant.

The (poly)alkylene glycol used in the present invention includes monoethylene glycol, diethylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, paraxylylene glycol, 1,4-cyclohexanemethanediol, etc. They may be used singly or in admixture of two or more.

The crystalline metallosilicate used in the present invention is a substance of regular porosity, having a particular crystal structure. That is, it is a solid substance having a large number of regularly arranged voids or pores and accordingly a large specific surface area.

The crystal line metallosilicate used in the present invention is crystalline aluminosilicate (which is generally called zeolite) or a compound wherein the Al atoms of crystalline aluminosilicate are replaced with other metal(s). Specific examples of the other metal(s) is (are) at least one of B, Ga, In, Ge, Sn, P, As, Sb, Sc, Y, La, Ti, Zr, V, Cr, Mn, Fe, Co, Ni, Cu, Zn, etc. Crystalline aluminosilicate, crystalline ferrosilicate, crystalline borosilicate and crystalline gallosilicate are preferred in view of the catalytic activity, the easiness of synthesis and the availability.

Specific examples of the crystalline metallosilicate used in the present invention are those metallosilicates having structures such as MFI (e.g. ZSM-5), MEL (e.g. ZSM-11), BEA (e.g. zeolite β), FAU (e.g. zeolite Y), MOR (e.g. mordenite), MTW (e.g. ZSM-12), LTL (e.g. Linde L) and the like (MFI, MEL, etc. are expressions according to IUPAC codes). The crystalline metallosilicate used in the present invention, also includes those metallosilicates having the structures described in, for example, "ZEOLITES, Vol. 12, No. 5, 1992" and "HANDBOOK OF MOLECULAR SIEVES, written by R. Szostak and published-from VAN NOSTRAND REINHOLD". These metallosilicates may be used singly or in combination of two or more. Of these metallosilicates, preferred are those having structures such as MFI and MEL (they are called pentasil type) or a BEA structure, for their excellent catalytic activities.

The crystalline metallosilicate used in the present invention, preferably has a silicon-to-metal atomic ratio of 5 to 1,500, particularly 10 to 500. A metallosilicate having a silicon-to-metal atomic ratio deviating from the above range has a low catalytic activity and is not preferred.

Many of the above crystalline metallosilicates contain ion-exchangeable cations outside their crystal lattices. The cations include $H^+$, $Li^+$, $Na^+$, $Rb^+$, $Cs^+$, $Mg^{2+}$, $Ca^{2+}$, $Sr^{2+}$, $Ba^{2+}$, $Sc^{3+}$, $Y^{3+}$, $La^{3+}$, $R_4N^+$, $R_4P^+$ (R is H or an alkyl group), etc. A metallosilicate wherein the part or whole of the cation is replaced with $H^+$, is preferred in the present invention.

The crystal line metallosilicate used in the present invention can be synthesized by a synthesis process used generally, for example, a hydrothermal synthesis process. Specifically, it can be synthesized by one of the processes described in Japanese Patent Publication No. 10064/1971; U.S. Pat. No. 3,965,207; "Journal of Molecular Catalysis", Vol. 31, pp. 355-370 (1985); etc. The crystalline metallosilicate can be synthesized, for example, by heating a composition (comprising a silica source, a metallo source and a quaternary ammonium salt such as tetrapropylammonium salt or the like), at a temperature of 100°-175° C. until a crystal is formed, then subjecting the solid product to filtration, washing with water and drying, and calcining the dried product at a temperature of 350°-600° C. As the silica source, there can be used water glass, silica sol, silica gel, an alkoxysilane, etc. As the metallo source, there can be used various inorganic or organic metal compounds. Preferred examples of the metal compounds are metal salts such as metal sulfate [e.g. $Al_2(SO_4)_3$], metal nitrate [e.g. $Fe(NO_3)_3$], alkali metal salt of metal oxide [e.g. $NaAlO_2$] and the like; metal halides such as metal chloride [e.g. $TiCl_4$], metal bromide [e.g. $MgBr_2$] and the like; and metal alkoxides [e.g. $Ti(OC_2H_5)_4$]. The crystalline metallosilicate obtained as above can be converted as necessary to an intended cation-containing metallosilicate. For example, a $H^+$-containing metallosilicate can be prepared by stirring a crystalline metallosilicate in an aqueous solution of HCl, $NH_4Cl$, $NH_3$ or the like to convert the cation contained in the metallosilicate, to $H^+$ or $NH_4^+$, then subjecting the resulting solid product to filtration, washing with water and drying, and calcining the dried product at a temperature of 350°-600° C. A metallosilicate containing an intended cation other than $H^+$ can be prepared by using an aqueous solution of the intended cation and subjecting a crystalline metallosilicate to the same procedure as above.

The catalyst used in the present invention may take any form such as powder, granules, molding of particular shape, or the like. When the catalyst is a molding, the molding may contain a carrier or binder such as alumina, silica, titania or the like.

In the present invention, the reaction between olefin and (poly)alkylene glycol can be conducted in the presence or absence of a solvent. As the solvent, there can be used nitromethane, nitroethane, nitrobenzene, dioxane, ethylene glycol dimethyl ether, sulfolane, benzene, toluene, xylene, hexane, cyclohexane, decane, paraffin, etc.

The reaction of the present invention has no particular restriction as to the manner and can be conducted in a manner used generally, for example, batchwise or continuously. The molar ratio of raw materials, i.e. olefin to (poly)alkylene glycol is not particularly restricted but is 0.05-20, preferably 0.1-10. The reaction temperature is 50°-250° C., preferably 100°-200° C. The reaction pressure may be any of reduced pressure, ordinary pressure and applied pressure, but is preferably ordinary pressure to 20 kg/cm².

When a batchwise reactor is used, the raw materials and catalyst of the present invention are fed into the reactor and stirring is conducted at a desired temperature and a desired pressure, whereby a reaction mixture containing an intended (poly)alkylene glycol monoalkyl ether is obtained. The amount of the catalyst used is not particularly restricted but is 0.1-100% by weight, preferably 0.5-50% by weight based on the olefin which is a raw material. The reaction time is 0.1-100 hours, preferably 0.5-30 hours although it varies depending upon the reaction temperature used, the amount of catalyst used, the amounts and kinds of raw materials used, etc. After the reaction, the catalyst is separated by centrifugation, filtration or the like and can be recycled for use in the next reaction. From the reaction mixture after catalyst separation can be recovered an intended (poly)alkylene glycol monoalkyl ether by extraction or distillation, and the unreacted raw materials can be recycled for use in the next reaction. Ordinarily, the (poly)alkylene glycol and the olefin (both are raw materials) have low solubilities in each other; the crystalline metallosilicate (catalyst) is contained in a (poly)alkylene glycol phase; and the (poly)alkylene glycol monoalkyl either (product) is contained in an olefin phase. Therefore, in the present process, the (poly)alkylene glycol phase and the olefin phase are separated from each other after the reaction; the (poly)alkylene glycol phase (which contains the catalyst) is mixed with a fresh (poly)alkylene glycol and can be recycled for use in the next reaction; and the olefin phase (which contains a product) is subjected to a separation procedure (e.g. distillation), whereby the raw material olefin and an intended product, i.e. a (poly)alkylene glycol monoalkyl ether can be recovered.

When a continuous reactor is used, the reaction can be conducted in any of a fluid bed type reactor, a fixed bed type reactor and a stirring tank type reactor. The reaction conditions differ depending upon the amounts and kinds of raw materials used, the concentration of catalyst used, the reaction temperature, etc., but the liquid hourly space velocity (LHSV), i.e. the value when the volume flow rate of raw materials is divided by the volume of reactor, is preferably 0.01-50 $hr^{-1}$, particularly 0.1-20 $hr^{-1}$. After the completion of the reaction, the reaction mixture is subjected to the same procedure as in using the batchwise reactor, whereby an intended (poly)alkylene glycol monoalkyl ether can be recovered.

The process of the present invention is characterized by reacting an olefin with a (poly)alkylene glycol in a liquid phase using a crystalline metallosilicate as a catalyst, to produce a (poly)alkylene glycol monoalkyl ether. In this process, the reaction rate between olefin and (poly)alkylene glycol is high and a (poly)alkylene glycol monoalkyl ether can be produced at a high conversion at a high selectivity. Therefore, the present process for production of (poly)alkylene glycol monoalkyl ether has very high industrial applicability.

The present invention is hereinafter described in more detail by way of Examples and Comparative Examples. However, the Examples represent only limited embodiments of the present invention, and the present invention is not restricted thereto.

In the Examples, the yields (mol %) of product and by-products were calculated using the following formulas.

---

Yield of monoethylene glycol monoalkyl ether (Y-EMA) =
[(moles of monoethylene glycol monoalkyl ether formed)/(moles of olefin fed)] × 100
Yield of diethylene glycol (Y-DEG) =
[(moles of diethylene glycol formed) × 2/

Yield of triethylene glycol (Y-TEG) =
[(moles of triethylene glycol formed) × 3/
(moles of monoethylene glycol fed)] × 100 /
[(moles of monoethylene glycol fed)] × 100

[Preparation of catalysts]

EXAMPLE 1

[Preparation of catalyst (1)]

The following solutions A and B were prepared.

| Solution A | |
|---|---|
| Water glass (JIS No. 3) | 55.6 g |
| Distilled water | 69.3 g |
| Solution B | |
| Anhydrous aluminum sulfate | 1.61 g |
| Concentrated sulfuric acid | 4.62 g |
| Tetrapropylammonium bromide | 6.95 g |
| Sodium chloride | 16.4 g |
| Distilled water | 94.6 g |

The solution B was placed in a 500-ml beaker and stirred. To the solution B being stirred was dropwise added the solution A to obtain a mixed gel. The mixed gel was fed into an autoclave; the gas space in the autoclave was replaced with nitrogen; and the autoclave contents were heated at 120° C. for 72 hours and then at 160° C. for 5 hours, with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 130° C. overnight and calcined in air at 550° C. to obtain a $Na^+$-containing crystalline aluminosilicate catalyst.

The catalyst was subjected to ion exchange using an aqueous ammonium chloride solution to convert to an $NH_4^+$-containing aluminosilicate catalyst. The catalyst was washed with water at 80° C. until no chlorine was detected, then dried at 130° C. overnight and calcined in air at 400° C. for 2 hours to obtain a catalyst (1).

The catalyst (1) was subjected to compositional analysis using a fluorescent X-ray, which showed a Si-to-Al atomic ratio of 26. The catalyst (1) had a specific surface area of 390 $m^2/g$. The catalyst (1) was a MFI type and the X-ray diffractometry result therefor was as shown in Table 1.

TABLE 1

X-ray diffractometry result of catalyst (1)

| 2θ | d (Å) | Relative intensity |
|---|---|---|
| 8.02 | 11.01 | 33 |
| 8.92 | 9.91 | 23 |
| 14.86 | 5.96 | 11 |
| 20.90 | 4.25 | 10 |
| 23.18 | 3.83 | 100 |
| 23.94 | 3.71 | 46 |
| 24.46 | 3.64 | 28 |
| 26.72 | 3.33 | 11 |
| 26.96 | 3.30 | 10 |
| 29.34 | 3.04 | 10 |
| 30.00 | 2.98 | 15 |

EXAMPLE 2

[Preparation of catalyst (2)]

The following solutions A', B' and C' were prepared.

| Solution A' | |
|---|---|
| Water glass (JIS No. 3) | 50.3 g |
| Distilled water | 24.3 g |
| Solution B' | |
| Anhydrous aluminum sulfate | 0.352 g |
| Concentrated sulfuric acid | 1.20 g |
| Distilled water | 20.0 g |
| Solution C' | |
| Tetrapropylammonium | 25.0 g |
| Distilled water | 40.0 g |

The solutions B' and C' were mixed with stirring, to prepare a uniform mixture. The mixture was placed in a 500-ml beaker and stirred vigorously using a ultradisperser. To the mixture being stirred was dropwise added the solution A' to obtain a mixed gel. The mixed gel was adjusted to pH 10.5 using sulfuric acid and fed into an autoclave. The gas space of the autoclave was replaced with nitrogen and the autoclave contents were heated at 120° C. for 48 hours with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 120° C. overnight and calcined in air at 560° C. to obtain a $Na^+$-containing crystalline aluminosilicate catalyst.

The catalyst was subjected to ion exchange using an aqueous ammonia solution to convert to an $NH_4^+$-containing aluminosilicate catalyst. The catalyst was dried at 120° C. overnight and calcined in air at 560° C. to obtain a catalyst (2).

The catalyst (2) was subjected to compositional analysis using a fluorescent X-ray, which showed a Si-to-Al atomic ratio of 120. The catalyst (2) had a specific surface area of 310 $m^2/g$. The catalyst (2) was a MFI type and the X-ray diffractometry result therefor was as shown in Table 2.

TABLE 2

X-ray diffractometry result of catalyst (2)

| 2θ | d (Å) | Relative intensity |
|---|---|---|
| 7.84 | 11.27 | 47 |
| 8.76 | 10.09 | 35 |
| 14.64 | 6.05 | 16 |
| 14.68 | 6.03 | 16 |
| 15.80 | 5.60 | 11 |
| 20.70 | 4.29 | 11 |
| 22.96 | 3.87 | 100 |
| 23.70 | 3.75 | 56 |
| 24.28 | 3.66 | 21 |
| 25.74 | 3.46 | 12 |
| 26.84 | 3.32 | 13 |
| 29.78 | 3.00 | 23 |
| 30.14 | 2.96 | 12 |
| 44.96 | 2.01 | 18 |
| 45.48 | 1.99 | 16 |

EXAMPLE 3

[Preparation of catalyst (3)]

A catalyst (3) was prepared in the same manner as in Example 2 except that the solution A' was changed to the following solution A".

| Solution A" | |
| --- | --- |
| Water glass (JIS No. 3) | 72.5 g |
| Distilled water | 35.0 g |

The catalyst (3) was subjected to compositional analysis using a fluorescent X-ray, which showed a Si-to-Al atomic ratio of 183. The catalyst (3) had a specific surface area of 170 m²/g. The catalyst (3) was a MFI type and the X-ray diffractometry result therefor was as shown in Table 3.

TABLE 3

X-ray diffractometry result of catalyst (3)

| 2θ | d (A) | Relative intensity |
| --- | --- | --- |
| 7.90 | 11.18 | 100 |
| 8.78 | 10.06 | 72 |
| 13.88 | 6.37 | 14 |
| 14.72 | 6.01 | 24 |
| 15.48 | 5.72 | 12 |
| 15.86 | 5.58 | 14 |
| 17.74 | 5.00 | 10 |
| 20.30 | 4.37 | 11 |
| 20.80 | 4.27 | 16 |
| 22.10 | 4.02 | 11 |
| 23.00 | 3.86 | 96 |
| 23.28 | 3.82 | 55 |
| 23.76 | 3.74 | 47 |
| 23.86 | 3.73 | 56 |
| 24.24 | 3.67 | 18 |
| 24.52 | 3.63 | 17 |
| 25.86 | 3.44 | 11 |
| 26.92 | 3.31 | 12 |
| 29.84 | 2.99 | 20 |
| 30.18 | 2.96 | 11 |

EXAMPLE 4
[Preparation of catalyst (4)]

The following solutions D, E and F were prepared.

| Solution D | |
| --- | --- |
| Water glass (JIS No. 3) | 69.0 g |
| Distilled water | 45.0 g |
| Solution E | |
| Iron (III) chloride hexahydrate | 3.60 g |
| Concentrated sulfuric acid | 6.20 g |
| Tetrapropylammonium bromide | 5.72 g |
| Distilled water | 60.0 g |
| Solution F | |
| Concentrated sulfuric acid | 1.80 g |
| Tetrapropylammonium bromide | 2.16 g |
| Distilled water | 208.0 g |
| Sodium chloride | 40.59 g |
| Sodium hydroxide | 2.39 g |

In a 500-ml beaker were mixed the solutions D, E and F for 20 minutes with vigorous stirring using a ultradisperser, to obtain a mixed gel. The mixed gel was adjusted to pH 10.5 using an aqueous sulfuric acid solution and fed into an autoclave. The gas space of the autoclave was replaced with nitrogen. The autoclave contents were heated to 160° C. in 90 minutes, then to 200° C. in 200 minutes, and kept at 200° C. for 50 minutes, with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 120° C. overnight and calcined in air at 540° C. for 3.5 hours to obtain a Na⁺-containing crystalline ferrosilicate catalyst.

The catalyst was subjected to ion exchange using an aqueous ammonia solution to convert to an $NH_4^+$-containing ferrosilicate catalyst. The catalyst was dried at 120° C. overnight and calcined in air at 540° C. to obtain a catalyst (4).

The catalyst (4) was subjected to compositional analysis using a fluorescent X-ray, which showed a Si-to-Fe atomic ratio of 10. The catalyst (4) was a MFI type and the X-ray diffractometry result therefor was as shown in Table 4.

TABLE 4

X-ray diffractometry result of catalyst (4)

| 2θ | d (A) | Relative intensity |
| --- | --- | --- |
| 7.86 | 11.24 | 68 |
| 8.76 | 10.09 | 48 |
| 13.86 | 6.38 | 11 |
| 14.74 | 6.00 | 18 |
| 15.44 | 5.73 | 10 |
| 15.84 | 5.59 | 13 |
| 20.78 | 4.27 | 11 |
| 23.04 | 3.86 | 100 |
| 23.86 | 3.73 | 49 |
| 24.34 | 3.65 | 27 |
| 29.86 | 2.99 | 15 |

EXAMPLE 5
[Preparation of catalyst (5)]

The following solutions G, H, I and J were prepared.

| Solution G | |
| --- | --- |
| Water glass (JIS No. 3) | 30.0 g |
| Distilled water | 14.5 g |
| Solution H | |
| Gallium nitrate octahydrate | 1.93 g |
| Distilled water | 20.0 g |
| Solution I | |
| Concentrated sulfuric acid | 0.50 g |
| Sodium chloride | 13.3 g |
| Distilled water | 40.0 g |
| Solution J | |
| Tetrapropylammonium bromide | 8.50 g |
| Distilled water | 20.0 g |

The solutions G and H were mixed with stirring, to prepare a uniform mixture. The mixture was placed in a 500-ml beaker and stirred vigorously using a ultradisperser. To the mixture being stirred were dropwise added the solution I and the solution J in this order. Then, stirring was continued for 1 hour to obtain a mixed gel. The mixed gel was adjusted to pH 10.5 using sulfuric acid and fed into an autoclave. The gas space of the autoclave was replaced with nitrogen. The autoclave contents were heated to 170° C. in 60 minutes and kept at 170° C. for 24 hours, with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 130° C. overnight and calcined in air at 550° C. for 5 hours to obtain a Na⁺-containing crystalline gallosilicate catalyst.

The catalyst was treated with 15 ml, per 1 g of the catalyst, of 2N aqueous ammonium chloride solution at 80° C. for 2 hours. This treatment was conducted three times, whereby the catalyst was ion-exchanged to convert to an $NH_4^+$-containing gallosilicate catalyst. The catalyst was washed with distilled water, dried at 130° C. overnight and calcined in air at 400° C. for 2 hours to obtain a catalyst (5).

The catalyst (5) was dissolved in hydrofluoric acid and subjected to compositional analysis by ICP atomic emission spectral analysis, which showed a Si-to-Ga atomic ratio of 28. The catalyst (5) was a MFI type and the X-ray diffractometry result therefor was as shown in Table 5.

TABLE 5

X-ray diffractometry result of catalyst (5)

| 2θ | d (Å) | Relative intensity |
|---|---|---|
| 7.86 | 11.24 | 70 |
| 8.76 | 10.09 | 45 |
| 9.00 | 9.82 | 15 |
| 13.84 | 6.39 | 13 |
| 14.72 | 6.01 | 19 |
| 15.44 | 5.73 | 10 |
| 15.82 | 5.60 | 14 |
| 20.78 | 4.27 | 14 |
| 23.02 | 3.86 | 100 |
| 23.62 | 3.76 | 32 |
| 23.86 | 3.73 | 47 |
| 24.32 | 3.66 | 32 |
| 26.86 | 3.32 | 11 |
| 29.20 | 3.06 | 11 |
| 29.84 | 2.99 | 15 |

EXAMPLE 6

[Preparation of catalyst (6)]

The following solutions K, L and M were prepared.

| Solution K | |
|---|---|
| Colloidal silica (Snowtex 30) | 36.0 g |
| Distilled water | 43.0 g |
| Sodium hydroxide | 2.73 g |
| Solution L | |
| Sodium aluminate | 0.50 g |
| Concentrated sulfuric acid | 0.90 g |
| Distilled water | 47.2 g |
| Solution M | |
| Tetrabutylammonium chloride | 5.0 g |
| Distilled water | 20.0 g |

The solutions L and M were mixed with stirring, to prepare a uniform mixture. The mixture was placed in a 500-ml beaker and stirred vigorously using a ultradisperser. To the mixture being stirred was dropwise added the solution K to obtain a mixed gel. The mixed gel was adjusted to pH 12.5 using concentrated sulfuric acid and fed into an autoclave. The gas space of the autoclave was replaced with nitrogen. The autoclave contents were heated at 150° C. for 120 hours with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 120° C. overnight and calcined in air at 560° C. for 3 hours to obtain a $Na^+$-containing crystalline aluminosilicate catalyst.

The catalyst was treated with 15 ml, per 1 g of the catalyst, of 2N aqueous ammonium chloride solution at 80° C. for 2 hours. This treatment was conducted three times, whereby the catalyst was ion-exchanged to convert to an $NH_4^+$-containing aluminosilicate catalyst. The catalyst was washed with distilled water, dried at overnight and calcined in air at 400° C. for 2 hours to obtain a catalyst (6).

The catalyst (6) was subjected to compositional analysis using a fluorescent X-ray, which showed a Si-to-Al atomic ratio of 55. The catalyst (6) was a MEL type and the X-ray diffractometry result therefor was as shown in Table 6.

TABLE 6

X-ray diffractometry result of catalyst (6)

| 2θ | d(Å) | Relative intensity |
|---|---|---|
| 7.90 | 11.18 | 100 |
| 8.78 | 10.06 | 63 |
| 14.76 | 6.00 | 24 |
| 15.88 | 5.58 | 15 |
| 23.10 | 3.85 | 99 |
| 23.92 | 3.72 | 47 |
| 24.32 | 3.66 | 11 |
| 29.92 | 2.98 | 13 |

EXAMPLE 7

[Preparation of catalyst (7)]

An MOR type zeolite [TSZ-650XOA (trade name), a product of Tosoh Corporation] was treated with 15 ml, per 1 g of the zeolite, of 6N hydrochloric acid at 100° C. for 3 hours, to remove part of the Al in zeolite. Then, washing with distilled water was conducted. The resulting material was dried at 120° C. overnight and calcined in air at 400° C. for 3 hours to obtain a catalyst (7).

The catalyst (7) was subjected to compositional analysis using a fluorescent X-ray, which showed a Si-to-Al atomic ratio of 39. The catalyst (7) had a specific surface area of 420 $m^2/g$. The catalyst (7) retained the MOR type and the X-ray diffractometry result therefor was as shown in Table 7.

TABLE 7

X-ray diffractometry result of catalyst (7)

| 2θ | d (Å) | Relative intensity |
|---|---|---|
| 6.46 | 13.67 | 19 |
| 8.66 | 10.20 | 26 |
| 9.66 | 9.15 | 82 |
| 13.46 | 6.57 | 61 |
| 13.94 | 6.35 | 15 |
| 15.22 | 5.82 | 25 |
| 19.64 | 4.52 | 54 |
| 22.44 | 3.96 | 81 |
| 23.32 | 3.81 | 19 |
| 23.74 | 3.74 | 13 |
| 25.74 | 3.46 | 100 |
| 26.42 | 3.37 | 49 |
| 27.26 | 3.27 | 12 |
| 27.66 | 3.22 | 52 |
| 31.00 | 2.88 | 19 |

EXAMPLE 8

[Preparation of catalyst (8)]

A FAU type zeolite [VALFOR CBV-780 (trade name), a product of PQ] was used as a catalyst (8). The catalyst (8) had a Si-to-Al atomic ratio of 40 and a specific surface area of 430 $m^2/g$.

EXAMPLE 9

[Preparation of catalyst (9)]

A BEA type zeolite [VALFOR CP 811BL-25 (trade name), a product of PQ] was used as a catalyst (9). The catalyst (9) had a Si-to-Al atomic ratio of 12.5 and a specific surface area of 750 m²/g.

EXAMPLE 10
[Preparation of catalyst (10)]

A BEA type zeolite [VALFOR CP 811BL-25 (trade name), a product of PQ] was treated with 15 ml, per 1 g of the zeolite, of 0.1N hydrochloric acid at 40° C. for 3 hours, to remove part of the Al in zeolite. Then, washing with distilled water was conducted. The resulting material was dried at 120° C. overnight and calcined in air at 400° C. for 3 hours to obtain a catalyst (10).

The catalyst (10) was subjected to compositional analysis using a fluorescent X-ray, which showed a Si-to-Al atomic ratio of 23. The catalyst (10) retained the BEA type and the X-ray diffractometry result therefor was as shown in Table 8.

TABLE 8

| X-ray diffractometry result of catalyst (10) | | |
|---|---|---|
| 2θ | d (Å) | Relative intensity |
| 7.66 | 11.53 | 70 |
| 21.30 | 4.17 | 20 |
| 22.34 | 3.98 | 100 |
| 25.22 | 3.53 | 10 |
| 26.96 | 3.30 | 11 |
| 28.72 | 3.11 | 10 |
| 29.50 | 3.03 | 10 |

EXAMPLE 11
[Preparation of catalyst (11)]

A BEA type zeolite [VALFOR CP 811BL-25 (trade name), a product of PQ] was treated with 15 ml, per 1 g of the zeolite, of 2N hydrochloric acid at 40° C. for 3 hours, to remove part of the Al in zeolite. Then, washing with distilled water was conducted. The resulting material was dried at 120° C. overnight and calcined in air at 400° C. for 3 hours to obtain a catalyst (11).

The catalyst (11) was subjected to compositional analysis using a fluorescent X-ray, which showed a Si-to-Al atomic ratio of 80. The catalyst (11) retained the BEA type by X-ray diffractometry.

EXAMPLE 12
[Preparation of catalyst (12)]

A BEA type zeolite [VALFOR CP 811BL-25 (trade name), a product of PQ] was treated with 15 ml, per 1 g of the zeolite, of 2N hydrochloric acid at 100° C. for 3 hours, to remove part of the Al in zeolite. Then, washing with distilled water was conducted. The resulting material was dried at 120° C. overnight and calcined in air at 400° C. for 3 hours to obtain a catalyst (12).

The catalyst (12) was subjected to compositional analysis using a fluorescent X-ray, which showed a Si-to-Al atomic ratio of 135. The catalyst (12) retained the BEA type by X-ray diffractometry.

EXAMPLE 13
[Preparation of catalyst (13)]

A BEA type zeolite [VALFOR CP 811BL-25 (trade name), a product of PQ] was treated with 15 ml, per 1 g of the zeolite, of 3N hydrochloric acid at 100° C. for 3 hours, to remove part of the Al in zeolite. Then, washing with distilled water was conducted. The resulting material was dried at 120° C. overnight and calcined in air at 400° C. for 3 hours to obtain a catalyst (13).

The catalyst (13) was subjected to compositional analysis using a fluorescent X-ray, which showed a Si-to-Al atomic ratio of 200. The catalyst (13) retained the BEA type by X-ray diffractometry.

EXAMPLE 14
[Preparation of catalyst (14)]

A BEA type zeolite [VALFOR CP 811BL-25 (trade name), a product of PQ] was treated with 15 ml, per 1 g of the zeolite, of 6N hydrochloric acid at 100° C. for 3 hours, to remove part of the Al in zeolite. Then, washing with distilled water was conducted. The resulting material was dried at 120° C. overnight and calcined in air at 400° C. for 3 hours to obtain a catalyst (14).

The catalyst (14) was subjected to compositional analysis using a fluorescent X-ray, which showed a Si-to-Al atomic ratio of 1,200. The catalyst (14) retained the BEA type by X-ray diffractometry.

EXAMPLE 15
[Preparation of catalyst (15)]

The following solutions N, O and P were prepared.

| Solution N | |
|---|---|
| Iron (III) nitrate nonahydrate | 6.7 g |
| Distilled water | 10.0 g |
| Solution O | |
| Tetraethyl silicate | 83.2 g |
| 20% aqueous tetraethylammonium hydroxide solution | 40.0 g |
| Solution P | |
| 20% aqueous tetraethylammonium hydroxide solution | 100.0 g |
| Sodium hydroxide | 1.6 g |

The solution N was placed in a 500-ml beaker and stirred vigorously using a ultradisperser. To the solution N being stirred were dropwise added the solution O and the solution P in this order to obtain a mixed gel. To the mixed gel was added, as seed crystals, 0.72 g of a BEA type zeolite [VALFOR CP 811BL-25 (trade name), a product of PQ]. The resulting mixture was adjusted to pH 13.1 using sulfuric acid, and heated at 60° C. for 24 hours to remove the ethanol contained therein. The resulting material was fed into an autoclave. The gas space of the autoclave was replaced with nitrogen. The autoclave contents were kept at 120° C. for 7 days with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 120° C. overnight and calcined in air at 550° C. for 3 hours to obtain a Na$^+$-containing crystalline ferrosilicate catalyst.

The catalyst was treated with 15 ml, per 1 g of the catalyst, of 1N aqueous ammonium chloride solution at 80° C. for 2 hours. This treatment was conducted three times, whereby the catalyst was ion-exchanged to convert to an NH$_4^+$-containing ferrosilicate catalyst. The catalyst was dried at 120° C. overnight and calcined in air at 400° C. for 2 hours. The catalyst after calcining was treated with 15 ml, per 1 g of the catalyst, of 1N hydrochloric acid at 40° C. for 3 hours to remove part of the Fe in ferrosilicate. The treated catalyst was washed with distilled water. The catalyst after washing was dried at 120° C. overnight and calcined in air at 400° C. for 2 hours to obtain a catalyst (15).

The catalyst (15) was subjected to compositional analysis using a fluorescent X-ray, which showed a Si-to-Fe atomic ratio of 22. The catalyst (15) was a BEA type and the X-ray diffractometry therefor was as shown in Table 9.

TABLE 9

X-ray diffractometry result of catalyst (15)

| 2θ | d (Å) | Relative intensity |
| --- | --- | --- |
| 7.16 | 12.34 | 47 |
| 7.68 | 11.50 | 74 |
| 21.36 | 4.16 | 16 |
| 22.38 | 3.97 | 100 |
| 25.28 | 3.52 | 11 |
| 26.90 | 3.31 | 12 |
| 28.72 | 3.11 | 10 |
| 29.50 | 3.03 | 10 |

EXAMPLE 16

[Preparation of catalyst (16)]

The following solutions Q and R were prepared.

| Solution Q | |
| --- | --- |
| Boric acid | 2.75 g |
| Sodium hydroxide | 4.61 g |
| Distilled water | 37.5 g |
| Solution R | |
| Tetraethylammonium bromide | 46.1 g |
| 28% aqueous ammonia solution | 72.1 g |
| Distilled water | 136.3 g |

The solution Q was placed in a 500-ml beaker and stirred vigorously using a ultradisperser. To the solution being stirred was dropwise added the solution R to obtain a mixed gel. The mixed gel was stirred for 15 minutes. Thereto was added 151.4 g of colloidal silica (Snowtex 30, a product of Nissan Chemical Industries, Ltd.), followed by stirring for 1 hour. To the resulting material was added, as seed crystals, 1.36 g of a BEA zeolite [VALFOR CP 811BL-25 (trade name), a product of PQ]. The mixture was adjusted to pH 12.9 using sulfuric acid and fed into an autoclave. The gas space of the autoclave was replaced with nitrogen. The autoclave contents were kept at 140° C. for 7 days with stirring.

The autoclave was cooled to room temperature. The reaction mixture containing a formed solid was taken out of the autoclave and subjected to decantation to remove the supernatant. The solid obtained was washed with distilled water to remove the ammonium salt. The solid after washing was dried at 120° C. overnight and calcined in air at 560° C. for 2 hours to obtain a $Na^+$-containing crystalline borosilicate catalyst.

The catalyst was treated with 20 ml, per 1 g of the catalyst, of 1N aqueous ammonium chloride solution at 80° C. for 2 hours. This treatment was conducted three times, whereby the catalyst was ion-exchanged to convert to an $NH_4^+$-containing borosilicate catalyst. The catalyst was dried at 120° C. overnight and calcined in air at 400° C. for 2 hours to obtain a catalyst (16).

The catalyst (16) was dissolved in hydrofluoric acid and subjected to compositional analysis by ICP atomic emission spectral analysis, which showed a Si-to-B atomic ratio of 37. The catalyst (16) was a BEA type and the X-ray diffractometry result therefor was as shown in Table 10.

TABLE 10

X-ray diffractometry result of catalyst (16)

| 2θ | d (Å) | Relative intensity |
| --- | --- | --- |
| 7.30 | 12.10 | 45 |
| 7.86 | 11.24 | 77 |
| 8.82 | 10.02 | 13 |
| 14.76 | 6.00 | 10 |
| 21.68 | 4.10 | 19 |
| 22.72 | 3.91 | 100 |
| 23.20 | 3.83 | 26 |
| 25.60 | 3.48 | 10 |
| 27.20 | 3.28 | 11 |
| 29.92 | 2.98 | 10 |

EXAMPLE 17

[Preparation of catalyst (17)]

The catalyst (10) prepared in Example 10 was treated and ion-exchanged with 10 ml, per 1 g of the catalyst, of 0.2N aqueous lanthanum nitrate solution at 80° C. for 2 hours to convert to a $La^{3+}$-containing catalyst. The catalyst was washed with distilled water. The catalyst after washing was dried at 120° C. overnight and calcined at 550° C. for 3 hours to obtain a catalyst (17).

The catalyst (17) was dissolved in hydrofluoric acid and subjected to compositional analysis by ICP atomic emission spectral analysis, which indicated an ion exchange ratio from $H^+$ to $La^{3+}$, of 35%. The catalyst (17) retained the BEA type by X-ray diffractometry.

EXAMPLE 18

[Preparation of catalyst (18)]

The catalyst (10) prepared in Example 10 was treated and ion-exchanged with 10 ml, per 1 g of the catalyst, of 0.0035N aqueous calcium nitrate solution at 80° C. for 3 hours to convert to a $Ca^{2+}$-containing catalyst. The catalyst was washed with distilled water. The catalyst after washing was dried at 120° C. overnight and calcined at 550° C. for 3 hours to obtain a catalyst (18).

The calcium concentrations of the aqueous calcium solutions before and after treatment were measured by ICP atomic emission spectral analysis, which indicated an ion exchange ratio from $H^+$ to $Ca^{2+}$, of 6%. The catalyst (18) retained the BEA type by X-ray diffractometry.

EXAMPLE 19

[Preparation of catalyst (19)]

The catalyst (10) prepared in Example 10 was treated and ion-exchanged with 10 ml, per 1 g of the catalyst, of 0.008N aqueous cesium chloride solution at 80° C. for 3 hours to convert to a $Cs^+$-containing catalyst. The catalyst was washed with distilled water. The catalyst after washing was dried at 120° C. overnight and calcined at 550° C. for 3 hours to obtain a catalyst (19).

The cesium concentrations of the aqueous cesium solutions before and after treatment were measured using a capillary type isotachophoresis analyzer, which indicated an ion exchange ratio from $H^+$ to $Cs^+$, of 10%. The catalyst (19) retained the BEA type by X-ray diffractometry.

[Production of (poly)alkylene glycol monoalkyl ethers]

EXAMPLE 20

60 g (0.36 mol) of 1-dodecene, 22 g (0.35 mol) of monoethylene glycol and 2.5 g of the catalyst (1) were fed into a 200-ml glass reactor equipped with a stirring blade and a reflux condenser. The gas space of the reactor was replaced with nitrogen, and the reactor inside was kept at ordinary pressure.

The reactor contents were heated to 150° C. with stirring at 650 rpm to give rise to a reaction at the same temperature for 2 hours. The reaction mixture was cooled to room temperature, and the olefin phase and the glycol phase were analyzed by gas chromatography.

The olefin phase contained monoethylene glycol monododecyl ether formed by the reaction, and the glycol phase contained diethylene glycol and triethylene glycol, which were each a dehydration and condensation product formed by the side reaction of monoethylene glycol. The results are shown in Table 11.

EXAMPLE 21–39

Reactions were conducted in the same manners as in Example 20 except that 2.5 g of one of the catalysts (1) to (19) shown in Table 11 was used in place of 2.5 g of the catalyst (1) and that the reaction temperature and the reaction time were changed to those shown in Table 11.

After each reaction, analysis was conducted in the same manner as in Example 20. The results are shown in Table 11.

TABLE 12

| | | | | Results of reaction | | |
|---|---|---|---|---|---|---|
| Example | Catalyst | Temp. (°C.) | Time (hr) | Y-EMA (mol %) | Y-DEG (mol %) | Y-TEG (mol %) |
| Example 40 | Catalyst (10) | 120 | 3 | 22.3 | 0.0 | 0.0 |
| Example 41 | Catalyst (10) | 135 | 3 | 37.3 | 0.0 | 0.0 |
| Example 42 | Catalyst (10) | 150 | 1.5 | 34.4 | 1.0 | 0.0 |

EXAMPLE 43

60 g (0.36 mol) of 1-dodecene, 22 g (0.35 mol) of monoethylene glycol, 42 g (0.35 mol) of sulfolane and 2.5 g of the catalyst (10) were fed into a 200-ml glass reactor equipped with a stirring blade and a reflux condenser. The gas space of the reactor was replaced with nitrogen, and the reactor inside was kept at ordinary pressure.

The reactor contents were heated to 150° C. with stirring at 650 rpm to give rise to a reaction at the same temperature for 3 hours. The reaction mixture was cooled to room temperature, and the monoethylene glycol monododecyl

TABLE 11

| | | | | | | | Results of reaction | | |
|---|---|---|---|---|---|---|---|---|---|
| Example | Catalyst | Crystal structure | Metal | Si/Metal (mol/mol) | Temp. (°C.) | Time (hr) | Y-EMA (mol %) | Y-DEG (mol %) | Y-TEG (mol %) |
| Example 20 | Catalyst (1) | MFI | Al | 26 | 150 | 2 | 9.5 | 0.9 | 0.0 |
| Example 21 | Catalyst (2) | MFI | Al | 120 | 150 | 2 | 2.1 | 0.3 | 0.0 |
| Example 22 | Catalyst (3) | MFI | Al | 183 | 150 | 4 | 0.3 | 0.2 | 0.0 |
| Example 23 | Catalyst (1) | MFI | Al | 26 | 185 | 1 | 15.0 | 3.7 | 0.2 |
| Example 24 | Catalyst (4) | MFI | Fe | 10 | 185 | 3 | 4.2 | 0.4 | 0.0 |
| Example 25 | Catalyst (5) | MFI | Ga | 28 | 185 | 3 | 9.4 | 8.2 | 0.8 |
| Example 26 | Catalyst (6) | MEL | Al | 55 | 185 | 3 | 8.3 | 10.0 | 0.7 |
| Example 27 | Catalyst (7) | MOR | Al | 39 | 185 | 3 | 1.5 | 1.0 | 0.0 |
| Example 28 | Catalyst (8) | FAU | Al | 40 | 185 | 3 | 4.2 | 0.8 | 0.0 |
| Example 29 | Catalyst (9) | BEA | Al | 12.5 | 150 | 3 | 11.4 | 1.7 | 0.1 |
| Example 30 | Catalyst (10) | BEA | Al | 23 | 150 | 3 | 29.8 | 1.9 | 0.0 |
| Example 31 | Catalyst (11) | BEA | Al | 80 | 150 | 3 | 22.2 | 4.3 | 0.2 |
| Example 32 | Catalyst (12) | BEA | Al | 135 | 150 | 3 | 15.4 | 3.0 | 0.1 |
| Example 33 | Catalyst (13) | BEA | Al | 200 | 150 | 3 | 17.9 | 1.1 | 0.0 |
| Example 34 | Catalyst (14) | BEA | Al | 1200 | 150 | 3 | 1.7 | 0.1 | 0.0 |
| Example 35 | Catalyst (15) | BEA | Fe | 22 | 150 | 3 | 1.5 | 0.2 | 0.0 |
| Example 36 | Catalyst (16) | BEA | B | 37 | 150 | 3 | 5.3 | 0.5 | 0.0 |
| Example 37 | Catalyst (17) | BEA | Al | 23 | 150 | 3 | 27.1 | 1.6 | 0.0 |
| Example 38 | Catalyst (18) | BEA | Al | 23 | 150 | 3 | 23.2 | 1.4 | 0.0 |
| Example 39 | Catalyst (19) | BEA | Al | 23 | 150 | 3 | 19.9 | 1.6 | 0.0 |

EXAMPLES 40–42

Reactions were conducted in the same manners as in Example 20 except that 66 g (1.06 mols) of monoethylene glycol was used in place of 22 g of monoethylene glycol, 7.5 g of the catalyst (10) was used in place of 2.5 g of the catalyst (1), and the reaction temperature and the reaction time were changed to those shown in Table 12.

After each reaction, analysis was conducted in the same manner as in Example 20. The results are shown in Table 12.

ether, diethylene glycol and triethylene glycol formed by the reaction were determined by gas chromatography. The results are shown in Table 13.

EXAMPLE 44

A reaction was conducted in the same manner as in Example 43 except that 60 g (0.35 mol) of dodecane was used in place of 42 g of sulfolane.

After the reaction, analysis was conducted in the same manner as in Example 43. The results are shown in Table 13.

EXAMPLE 45

A reaction was conducted in the same manner as in Example 43 except that 216 g (2.45 mols) of dioxane was used in place of 42 g of sulfolane and that the reaction time was changed to 6 hours. After the reaction, analysis was conducted in the same manner as in Example 43. The results are shown in Table 13.

TABLE 13

| Example | Catalyst | Solvent | Temp. (°C.) | Time (hr) | Y-EMA (mol %) | Y-DEG (mol %) | Y-TEG (mol %) |
|---|---|---|---|---|---|---|---|
| Example 43 | Catalyst (10) | Sulfolane | 150 | 3 | 24.7 | 1.3 | 0.1 |
| Example 44 | Catalyst (10) | Dodecane | 150 | 3 | 15.6 | 2.9 | 0.1 |
| Example 45 | Catalyst (10) | Dioxane | 150 | 6 | 13.2 | — | — |

Comparative Example 1

A reaction was conducted in the same manner as in Example 20 except that 2.5 g of a strongly acidic cation exchange resin (Nafion NR-50, a product of DuPont) was used in place of 2.5 g of the catalyst (1) and that the reaction time was changed to 4 hours.

After the reaction, analysis was conducted in the same manner as in Example 20. The results are shown in Table 14.

Comparative Example 2

A reaction was conducted in the same manner as in Example 20 except that 0.84 g of a strongly acidic cation exchange resin (Amberlyst 15, a product of Rohm and Haas) was used in place of 2.5 g of the catalyst (1) and that the reaction time was changed to 4 hours.

After the reaction, analysis was conducted in the same manner as in Example 20. The results are shown in Table 14.

Comparative Example 3

A reaction was conducted in the same manner as in Example 20 except that 0.8 g of benzenesulfonic acid was used in place of 2.5 g of the catalyst (1) and that the reaction time was changed to 12 hours.

After the reaction, analysis was conducted in the same manner as in Example 20. The results are shown in Table 14.

Comparative Example 4

A reaction was conducted in the same manner as in Example 43 except that 3.2 g of amorphous silica alumina (N631HN, a product of Nikki Chemical Co., Ltd.) was used in place of 2.5 g of the catalyst (10) and that the reaction time was changed to 4 hours.

After the reaction, analysis was conducted in the same manner as in Example 43. The results are shown in Table 14.

used in place of 2.5 g of the catalyst (1), and the reaction time was changed to 3 hours.

After the reaction, analysis was conducted in the same manner as in Example 20. The results are shown in Table 15.

EXAMPLE 47

A reaction was conducted in the same manner as in Example 20 except that 78 g (0.35 mol) of 1-hexadecene was used in place of 60 g of 1-dodecene, 2.5 g of the catalyst (10) was used in place of 2.5 g of the catalyst (1), and the reaction time was changed to 6 hours.

After the reaction, the monoethylene glycol monohexadecyl ether, diethylene glycol and triethylene glycol formed by the reaction were determined in the same manners as in Example 20. The results are shown in Table 15.

EXAMPLE 48

A reaction was conducted in the same manner as in Example 20 except that 88 g (0.35 mol) of 1-octadecene was used in place of 60 g of 1-dodecene, 2.5 g of the catalyst (10) was used in place of 2.5 g of the catalyst (1), and the reaction time was changed to 6 hours.

After the reaction, the monoethylene glycol monooctadecyl ether, diethylene glycol and triethylene glycol formed by the reaction were determined in the same manners as in Example 20. The results are shown in Table 15.

TABLE 14

| Comparative Example | Catalyst | Solvent | Temp. (°C.) | Time (hr) | Y-EMA (mol %) | Y-DEG (mol %) | Y-TEG (mol %) |
|---|---|---|---|---|---|---|---|
| Comparative Example 1 | Nafion NR-50 | — | 150 | 4 | 2.4 | 15.5 | 1.5 |
| Comparative Example 2 | Amberlyst 15 | — | 150 | 4 | 0.4 | 19.4 | 1.8 |
| Comparative Example 3 | Benzenesulfonic acid | — | 150 | 12 | 1.4 | 22.1 | 5.0 |
| Comparative Example 4 | Silica alumina | Sulfolane | 150 | 4 | 0.0 | 0.0 | 0.0 |

EXAMPLE 46

A reaction was conducted in the same manner as in Example 20 except that 60 g of inner dodecene (which contained 1.8 mol % of 1-dodecene as an impurity) was used in place of 60 g of 1-dodecene, 2.5 g of the catalyst (10) was

TABLE 15

| | | | | | Results of reaction | | |
| --- | --- | --- | --- | --- | --- | --- | --- |
| Example | Catalyst | Olefin | Temp. (°C.) | Time (hr) | Y-EMA (mol %) | Y-DEG (mol %) | Y-TEG (mol %) |
| Example 46 | Catalyst (10) | In-$C_{12}$ | 150 | 3 | 7.3 | 1.4 | 0.0 |
| Example 47 | Catalyst (10) | α-$C_{16}$ | 150 | 6 | 27.5 | 5.8 | 0.4 |
| Example 48 | Catalyst (10) | α-$C_{18}$ | 150 | 6 | 17.2 | 6.7 | 0.5 |

What is claimed is:

1. A process for producing a (poly)alkylene glycol monoalkyl ether, which comprises reacting an olefin with a (poly)alkylene glycol in the presence of a crystalline metallosilicate as a catalyst, wherein part or all of the cation is replaced with $H^+$.

2. A process according to claim 1, wherein the olefin is at least one member selected from the group consisting of noncyclic olefins having 6 to 30 carbon atoms.

3. A process according to claim 1, wherein the crystalline metallosilicate contains at least one metal element selected from the group consisting of Al, Fe, Ga and B.

4. A process according to claim 1 or 3, wherein the crystalline metallosilicate is a pentasil metallosilicate.

5. A process according to claim 1 or 3, wherein the crystalline metallosilicate is a BEA metallosilicate.

6. A process according to claims 1 or 2, wherein the crystalline metallosilicate has a silicon-to-metal atomic ratio of 5 to 1,500.

7. A process according to claims 1, 2 or 3, wherein the reaction is conducted in a liquid phase.

* * * * *